US012616828B2

(12) United States Patent
Mathiesen et al.

(10) Patent No.: US 12,616,828 B2
(45) Date of Patent: May 5, 2026

(54) DETECTING HEATING OF IMPLANTED COIL HERMETIC PACKAGE WHEN MISALIGNED

(71) Applicant: Boston Scientific Scimed, Inc., Maple Grove, MN (US)

(72) Inventors: Danielle S. Mathiesen, North Branch, MN (US); Eric A. Schilling, Ham Lake, MN (US); David J. Peichel, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 330 days.

(21) Appl. No.: 18/251,367

(22) PCT Filed: Sep. 22, 2021

(86) PCT No.: PCT/US2021/051442
§ 371 (c)(1),
(2) Date: May 1, 2023

(87) PCT Pub. No.: WO2022/103490
PCT Pub. Date: May 19, 2022

(65) Prior Publication Data
US 2023/0414926 A1     Dec. 28, 2023

Related U.S. Application Data

(60) Provisional application No. 63/112,270, filed on Nov. 11, 2020.

(51) Int. Cl.
*A61M 60/875*     (2021.01)
*H02J 50/90*     (2016.01)

(52) U.S. Cl.
CPC ........... *A61M 60/875* (2021.01); *H02J 50/90* (2016.02); *A61M 2205/8243* (2013.01); *H02J 2310/23* (2020.01)

(58) Field of Classification Search
CPC . A61N 1/3787; A61M 60/871; A61M 60/873; A61M 60/875
See application file for complete search history.

(56) References Cited

U.S. PATENT DOCUMENTS

| | | | |
|---|---|---|---|
| 7,774,069 B2 | 8/2010 | Olson et al. | |
| 7,997,854 B2 | 8/2011 | LaRose et al. | |

(Continued)

FOREIGN PATENT DOCUMENTS

| | | |
|---|---|---|
| EP | 3591805 A1 | 1/2020 |
| WO | 2015018868 A1 | 2/2015 |
| WO | 2022103490 A1 | 5/2022 |

OTHER PUBLICATIONS

International Preliminary Report on Patentability from International Application No. PCT/US2021/051442 dated May 16, 2023, 6 pp.

(Continued)

*Primary Examiner* — Allen Porter
(74) *Attorney, Agent, or Firm* — Seager, Tufte & Wickhem LLP

(57) ABSTRACT

A method of monitoring heating of a hermetic package of an implanted transcutaneous energy transfer system (TETS) coil, the method includes monitoring a power transfer between the implanted TETS coil and an external TETS coil; detecting an amount of power lost during the power transfer; determining if the amount of power lost during the power transfer is above a first predetermined threshold; if the power lost is above the first predetermined threshold, determining if a misalignment between the implanted TETS coil and the external TETS coil is greater than a predetermined distance; and if the misalignment is greater than the predetermined distance, generating an alert to align the external TETS coil with the implanted TETS coil.

19 Claims, 3 Drawing Sheets

(56) References Cited

U.S. PATENT DOCUMENTS

| | | | |
|---|---|---|---|
| 8,419,609 | B2 | 4/2013 | Shambaugh, Jr. et al. |
| 8,700,175 | B2 | 4/2014 | Fell |
| 8,818,523 | B2 | 8/2014 | Olson et al. |
| 9,404,954 | B2 | 8/2016 | Roy et al. |
| 11,191,973 | B2 | 12/2021 | Escalona et al. |
| 11,331,500 | B1 * | 5/2022 | Perryman ............ A61N 1/3787 |
| 2005/0075697 | A1 | 4/2005 | Olson et al. |
| 2011/0128015 | A1 | 6/2011 | Dorairaj et al. |
| 2011/0196544 | A1 | 8/2011 | Baaman et al. |
| 2012/0139485 | A1 | 6/2012 | Olson et al. |
| 2013/0127259 | A1 | 5/2013 | Lohr et al. |
| 2013/0241302 | A1 | 9/2013 | Miyamoto et al. |
| 2015/0222127 | A1 | 8/2015 | Hansen |
| 2015/0283313 | A1 | 10/2015 | Huber |
| 2015/0290373 | A1 | 10/2015 | Rudser et al. |
| 2017/0201130 | A1 | 7/2017 | Park |
| 2019/0111198 | A1 | 4/2019 | Bluvshtein et al. |
| 2019/0214830 | A1 | 7/2019 | Hansen |
| 2019/0296588 | A1 | 9/2019 | Muratov |
| 2019/0312467 | A1 | 10/2019 | Mynar et al. |
| 2021/0226667 | A1 | 7/2021 | Swaans et al. |
| 2021/0283392 | A1 | 9/2021 | Schilling et al. |
| 2022/0062516 | A1 | 3/2022 | Peichel et al. |

OTHER PUBLICATIONS

International Search Report and Written Opinion of International Application No. PCT/US2021/051442 dated Jan. 5, 2022, 9 pp.
Office Action from U.S. Appl. No. 17/008,752 dated Aug. 25, 2022, 11 pp.

* cited by examiner

DETECTING HEATING OF IMPLANTED COIL HERMETIC PACKAGE WHEN MISALIGNED

This application is a U.S. National Stage entry under 35 U.S.C. § 371 of International Application No. PCT/US2021/051442, filed Sep. 22, 2021, which claims priority from and the benefit of U.S. Provisional Patent Application No. 63/112,270, filed on Nov. 11, 2020, the entire content of each of which is incorporated herein by reference.

FIELD

The present technology is generally related to a method and controller for monitoring heating of a hermetic package of an implanted transcutaneous energy transfer system (TETS) coil.

BACKGROUND

Implanted TETS coils for wireless power transfer including tuning capacitors that are disposed in a hermetic package coupled to the implanted TETS coil. However, if an external coil of the TETS becomes misaligned with the implanted TETS coil, high levels of heating of the hermetic package may exceed thermal requirements.

SUMMARY

The techniques of this disclosure generally relate to a method and controller for monitoring heating of a hermetic package of an implanted transcutaneous energy transfer system (TETS) coil In one aspect, the present disclosure provides a method of monitoring heating of a hermetic package of an implanted transcutaneous energy transfer system (TETS) coil, the method includes monitoring a power transfer between the implanted TETS coil and an external TETS coil; detecting an amount of power lost during the power transfer; determining if the amount of power lost during the power transfer is above a first predetermined threshold; if the power lost is above the first predetermined threshold, determining if a misalignment between the implanted TETS coil and the external TETS coil is greater than a predetermined distance; and if the misalignment is greater than the predetermined distance, generating an alert to align the external TETS coil with the implanted TETS coil.

In another aspect of this embodiment, if the misalignment is less than the predetermined distance, generating an alert to a presence of a foreign object.

In another aspect of this embodiment, if following the generating of the alert to align the external TETS coil with the implanted TETS coil the coil misalignment is less than the predetermined distance, the method further includes continuing to monitor the power transfer.

In another aspect of this embodiment, if following the generating of the alert to align the external TETS coil with the implanted TETS coil, the coil misalignment is greater than the predetermined distance, the method further includes determining if the misalignment has improved within a first predetermined period of time.

In another aspect of this embodiment, the method further includes reducing or stopping charging a battery of an internal controller of an implanted blood pump in communication with the implanted TETS if the misalignment has not improved within the first predetermined period of time.

In another aspect of this embodiment, the method further includes generating the alert to align the external TETS coil with the implanted TETS coil following the reducing or stopping the charging of the battery.

In another aspect of this embodiment, if following the generating of the alert to align the external TETS coil with the implanted TETS coil the coil misalignment is greater than the predetermined distance, the method further includes determining if the misalignment has improved within a second predetermined period of time greater than the first predetermined period of time and if the amount of power lost is greater than a second predetermined threshold, the method further includes suspending the transfer of power between the external TETS coil and the implanted TETS coil.

In another aspect of this embodiment, the predetermined distance is 3 cm.

In another aspect of this embodiment, the first predetermined threshold and the second predetermined threshold between is 100-500 mW.

In another aspect of this embodiment, the first predetermined period of time is between 1-5 minutes.

In another aspect of this embodiment, the second predetermined period of time is between 2-10 minutes.

In one aspect, a controller for an implantable blood pump includes processing circuitry configured to monitor a power transfer between the implanted TETS coil and an external TETS coil; detect an amount of power lost during the power transfer; determine if the amount of power lost during the power transfer is above a first predetermined threshold; if the power lost is above the first predetermined threshold, determine if a misalignment between the implanted TETS coil and the external TETS coil is greater than a predetermined distance; and if the misalignment is greater than the predetermined distance, generate an alert to align the external TETS coil with the implanted TETS coil.

In another aspect of this embodiment, if the misalignment is less than the predetermined distance, the processing circuitry is further configured to generate an alert to a presence of a foreign object.

In another aspect of this embodiment, if following the generating of the alert to align the external TETS coil with the implanted TETS coil the coil misalignment is less than the predetermined distance, the processing circuitry is further configured to monitor the power transfer.

In another aspect of this embodiment, if following the generating of the alert to align the external TETS coil with the implanted TETS coil, the coil misalignment is greater than the predetermined distance, the processing circuitry is further configured to determine if the misalignment has improved within a first predetermined period of time.

In another aspect of this embodiment, the processing circuitry is further configured to reduce or stop charging a battery of an internal controller of an implanted blood pump in communication with the implanted TETS if the misalignment has not improved within the first predetermined period of time.

In another aspect of this embodiment, the processing circuitry is further configured to generate the alert to align the external TETS coil with the implanted TETS coil following the reducing or stopping the charging of the battery.

In another aspect of this embodiment, if following the generating of the alert to align the external TETS coil with the implanted TETS coil the coil misalignment is greater than the predetermined distance, the processing circuitry is further configured to determine if the misalignment has improved within a second predetermined period of time greater than the first predetermined period of time and if the amount of power lost is greater than a second predetermined threshold, the processing circuitry is further configured to suspend the transfer of power between the external TETS coil and the implanted TETS coil.

In another aspect of this embodiment, the predetermined distance is 3 cm.

In one aspect, a method of monitoring heating of a hermetic package of an implanted transcutaneous energy transfer system (TETS) coil includes monitoring a power transfer between the implanted TETS coil and an external TETS coil; detecting an amount of power lost during the power transfer; determining if the amount of power lost during the power transfer is above 200-300 mW; if the power lost is above 200-300 mW, determining if a misalignment between the implanted TETS coil and the external TETS coil is greater than 3 cm; and if the misalignment is greater than the 3 cm, generating an alert to align the external TETS coil with the implanted TETS coil.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
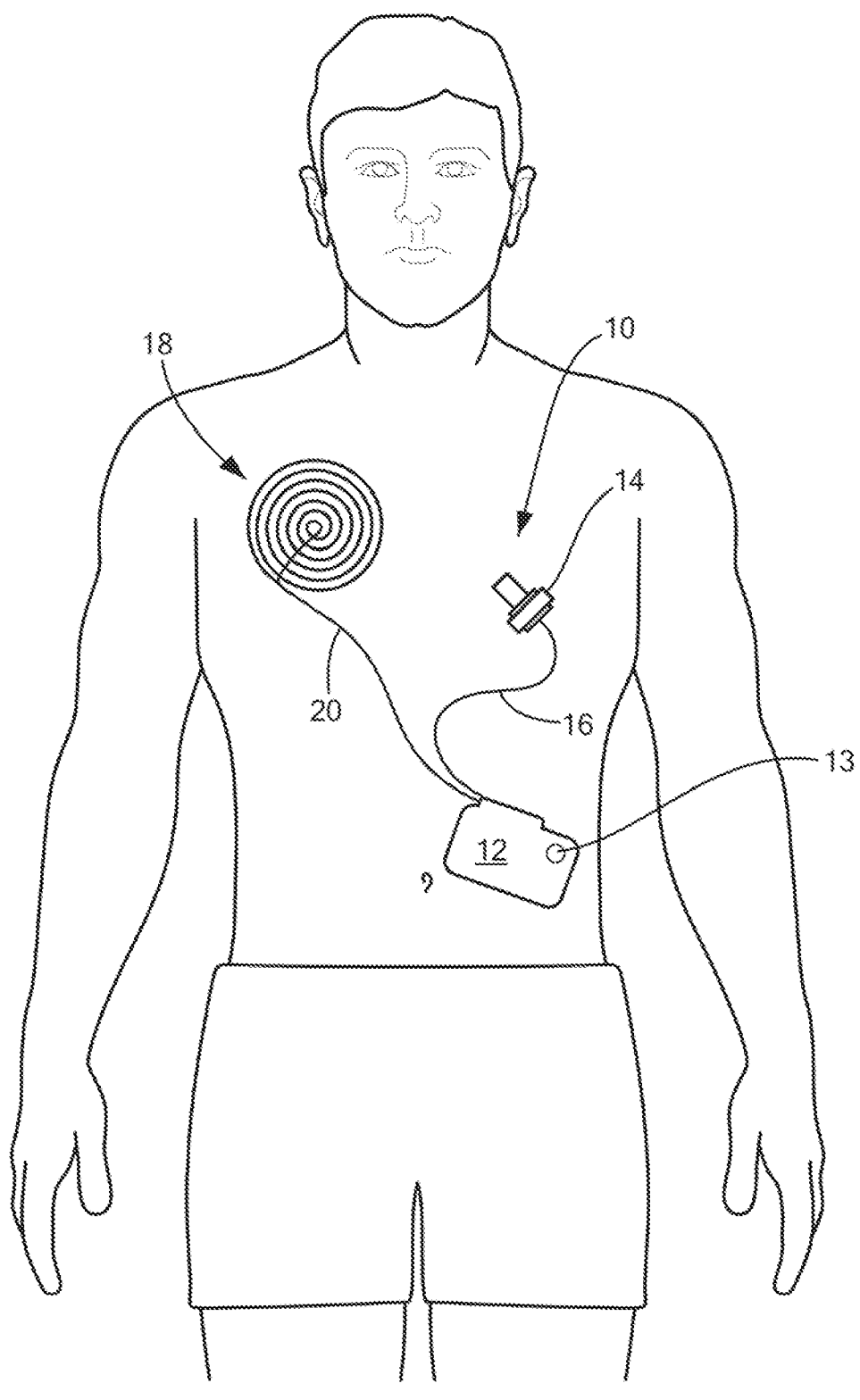
FIG. 1 is an internal system view of an implantable blood pump with a TETS receiver source constructed in accordance with the principles of the present application.
Figure 2:
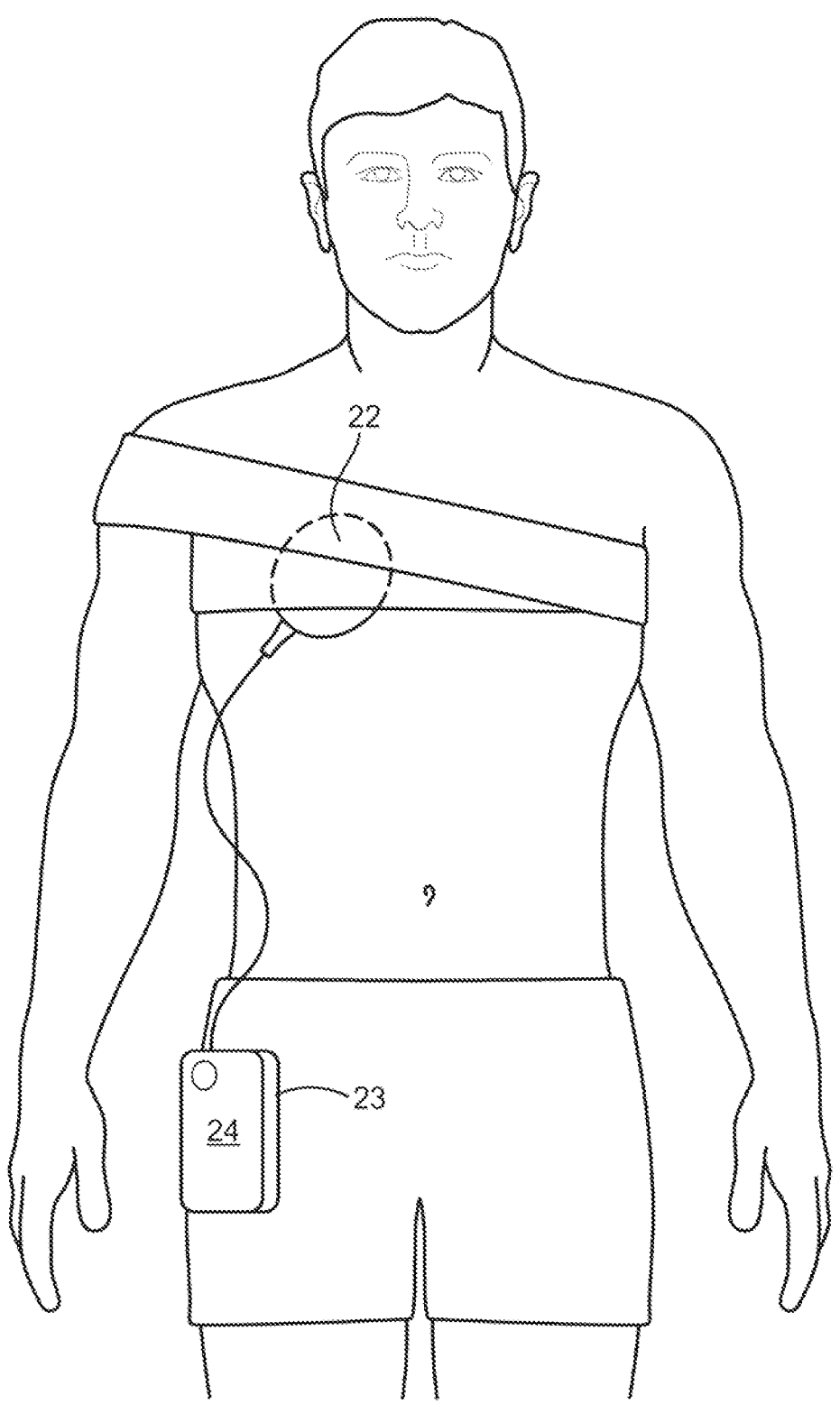
FIG. 2 is an external view of a TETS transmitter and a controller of the system shown in FIG. 1.

Referring now to the drawings in which like reference designators refer to like elements there is shown in FIGS. 1 and 2 an exemplary mechanical circulatory support device ("MCSD") constructed in accordance with the principles of the present application and designated generally as "10." The MCSD 10 may be fully implantable within a patient, whether human or animal, which is to say there are no percutaneous connections between the implanted components of the MCSD 10 and the components outside of the body of the patient. In the configuration shown in FIG. 1, the MCSD 10 includes an internal controller 12 implanted within the body of the patient. The internal controller 12 includes a control circuit having processing circuitry configured to control operation of an implantable blood pump 14. The internal controller 12 may include an internal power source 13, configured to power the components of the controller and provide power to one or more implantable medical devices, for example, the implantable blood pump, such as a ventricular assist device ("VAD") 14 implanted within the left ventricle of the patient's heart. The power source 13 may include a variety of different types of power sources including an implantable battery. VADs 14 may include centrifugal pumps, axial pumps, or other kinds electromagnetic pumps configured to pump blood from the heart to blood vessels to circulate around the body. One such centrifugal pump is the HVAD and is shown and described in U.S. Pat. No. 7,997,854, the entirety of which is incorporated by reference. One such axial pump is the MVAD and is shown and described in U.S. Pat. No 8,419,609. In an exemplary configuration, the VAD 14 is electrically coupled to the internal controller 12 by one or more implanted conductors 16 configured to provide power to the VAD 14, relay one or more measured feedback signals from the VAD 14, and/or provide operating instructions to the VAD 14.

Continuing to refer to FIG. 1, a receiving or implanted coil 18 may also be coupled to the internal controller 12 by, for example, one or more implanted conductors 20. In an exemplary configuration, the receiving coil 18 may be implanted subcutaneously proximate the thoracic cavity, although any subcutaneous position may be utilized for implanting the receiving coil 18. The receiving coil 18 is configured to be inductively powered through the patient's skin by a transmission or external coil 22 (seen in FIG. 2) disposed opposite the receiving coil 18 on the outside/exterior of the patient's body. For example, as shown in FIG. 2, a transmission coil 22 may be coupled to an external controller 23 having a power source 24, for example, a portable battery carried by the patient or wall power. In one configuration, the battery is configured to generate a radiofrequency signal for transmission of energy from the transmission coil 22 to the receiving coil 18. The receiving coil 18 may be configured for transcutaneous inductive communication with the transmission coil 22 to define a transcutaneous energy transfer system (TETS) that receives power from the transmission coil 22.

Figure 3:
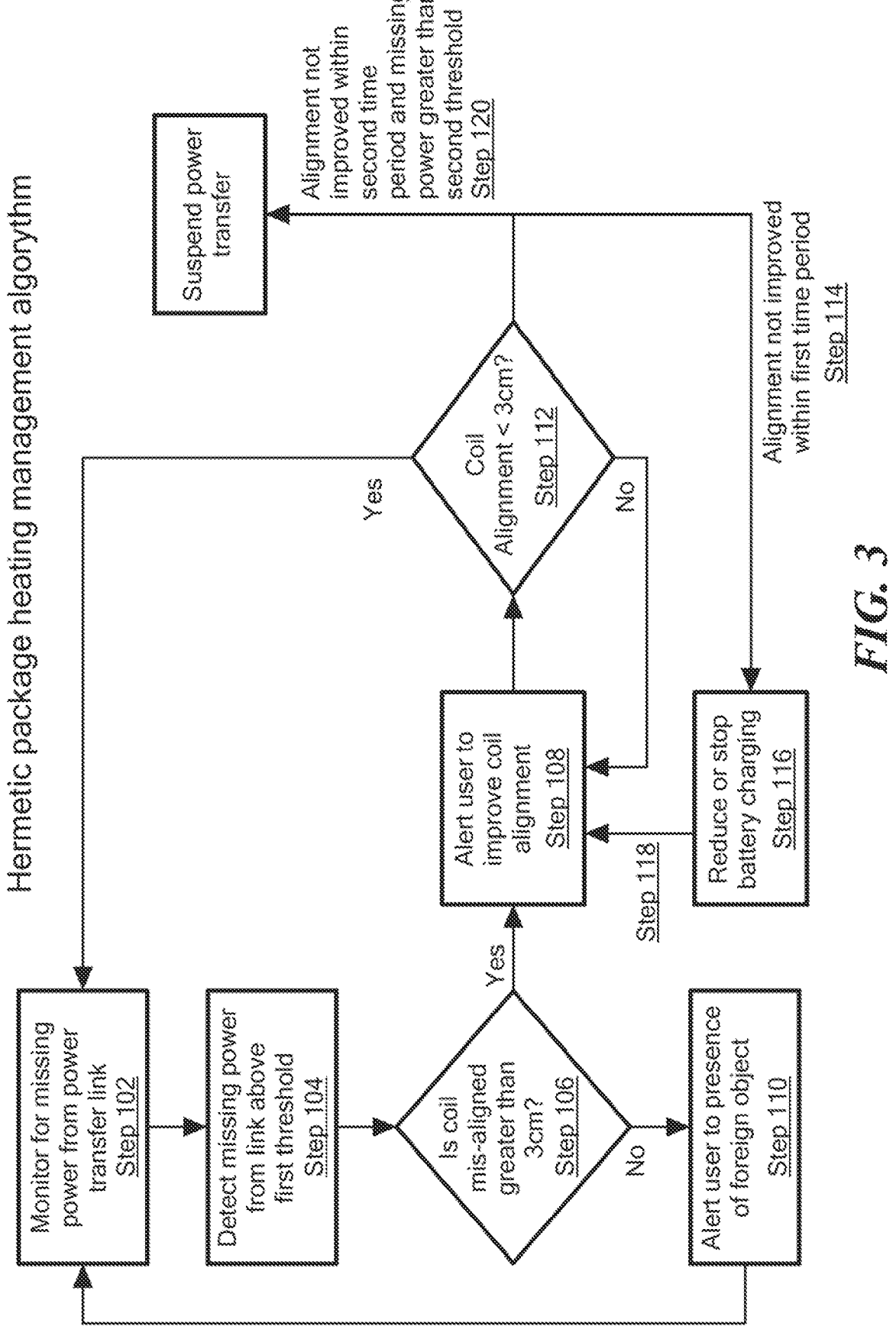
FIG. 3 is a block diagram illustrating the various steps of the disclosure of the application.

Referring now to FIG. 3 in which an exemplary flow chart of monitoring heating of a hermetic package of an implanted TETS coil 18 is show. The method includes monitoring a power transfer between the implanted TETS coil and an external TETS coil (Step 102). An amount of power lost during the power transfer is the detected (Step 104). In one configuration, the power lost during the power transfer is measured using a power accounting algorithm as between the external coil 22 and the implanted could 18 or by using a transfer function. Power lost may be a function of the coils being misaligned or by the presence of a transient foreign metallic object. The method further includes determining if the amount of power lost during the power transfer is above a first predetermined threshold (Step 104). In an exemplary configuration, the first predetermined threshold is 200-300 mW. If the power lost is above the first predetermined threshold, the method further includes determining if a misalignment between the implanted TETS coil 18 and the external TETS coil 22 is greater than a predetermined distance (Step 106). For example, using a transfer function, or by monitoring the power transfer efficiency, a misalignment distance can be determined. In an exemplary configuration, the predetermined misalignment distance is 3 cm or greater, although in other configurations, the distance may be as little is 1 cm or greater. If the misalignment is greater than the predetermined distance, an alert, which may be visual, audio, or tactile, is generated by the external controller 23 to align the external TETS coil 22 with the implanted TETS coil 18 (Step 108). However, if the misalignment is less than the predetermined distance, the alert is generated to indicate a presence of a foreign metallic object (Step 110). If following the generating of the alert to align the external TETS coil 22 with the implanted TETS 18 coil, the coil misalignment is less than the predetermined distance, then power monitoring is continued by the external controller 23 (Step 112). For example, if the patient has realigned the coils following the alert such that the misalignment is less than the predetermined distance, then the power transfer between the two coils is continued to be monitored. However, if following the generating of the alert to align the external TETS coil 22 with the implanted TETS coil 18, the coil misalignment is still greater than the predetermined distance, then the external controller 23 determines is the misalignment has improved within a first predetermined period of time (Step 114). For example, the controller 23 may monitor the power efficiency or use a transfer function to determine if within a first predetermined period of time, for example, 5 minutes, the misalignment has improved. For example, if the misalignment was 3 cm, if within 5 minutes the misalignment has not improved, the controller 23 is configured to reduce or stop charging a battery 13 of the internal controller 12 of the implanted blood pump 14 in communication with the implanted TETS 18 if the misalignment has not improved within the first predetermined period of time (Step 116).

Moreover, following the reducing or stopping the charging of the battery 13, the controller 23 is configured to generate the alert to the patient to align the external TETS coil 22 with the implanted TETS coil 18 (Step 118). However, if following the generating of the alert to align the external TETS coil 22 with the implanted TETS coil 18 the coil misalignment is still greater than the predetermined distance, the controller 23 is configured to determine if the misalignment has improved within a second predetermined period of time greater than the first predetermined period of time. In an exemplary configuration, the second predetermined period of time is 10 minutes, but may be any duration. If the amount of power lost is greater than a second predetermined threshold less than the first predetermined threshold, then the controller 23 is configured to suspend the transfer of power between the external TETS coil 22 and the implanted TETS coil 22 (Step 120). For example, if following the alert to align the coils the amount of power lost is still greater than, for example, 200-300 mW, then the foreign object may still be present and/or the coils are misaligned beyond the predetermined distance and thus power transfer between the coils is suspending to prevent overheating of the hermetic package.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of monitoring heating of a hermetic package of an implanted transcutaneous energy transfer system (TETS) coil, comprising:
   monitoring a power transfer between the implanted TETS coil and an external TETS coil;
   detecting an amount of power lost during the power transfer that is above a first predetermined threshold;
   generating an alert and initiating a first predetermined period of time in response to detecting that the amount of power lost is above the first predetermined threshold;
   monitoring the power transfer during the first predetermined period of time,
   determining that the power transfer has not improved during the first predetermined period of time;
   reducing a charging rate of a battery of an internal controller of an implanted blood pump in communication with the implanted TETS coil and initiating a second predetermined period of time in response to determining that the power transfer has not improved during the first predetermined period of time;
   monitoring the power transfer during the second predetermined period of time;
   determining that the power transfer has not improved during the second predetermined period of time; and
   suspending the power transfer between the external TETS coil and the implanted TETS coil based on determining that the power transfer has not improved during the second predetermined period of time.

2. The method of claim 1, wherein the first predetermined threshold is 100 mW to 500 mW.

3. The method of claim 1, wherein the first predetermined period of time is 1 minute to 5 minutes.

4. The method of claim 1, wherein the second predetermined period of time is 2 minutes to 10 minutes.

5. The method of claim 1, wherein the power lost is a function of the implanted TETS coil and the external TETS coil being misaligned.

6. The method of claim 1, wherein the power lost is a function of a presence of foreign metallic object between the implanted TETS coil and the external TEST coil.

7. The method of claim 1, wherein the power lost exceeding the first determined threshold occurs when a misalignment between the implanted TETS coil and the TETS coil is a distance of 3 centimeters or greater.

8. The method of claim 1, wherein the power lost exceeding the first determined threshold occurs when a misalignment between the implanted TETS coil and the TETS coil is a distance of 1 centimeters or greater.

9. The method of claim 1, wherein the first predetermined period of time is 5 minutes, and the second predetermined period of time is 10 minutes.

10. The method of claim 1, wherein the first predetermined threshold is 200-300 mW.

11. The method of claim 1, wherein generating the alert comprises generating a visual, audio, or tactile alert.

12. A controller for an implantable blood pump, comprising: processing circuitry configured to:

monitor a power transfer between the implanted TETS coil and an external TETS coil;

detect an amount of power lost during the power transfer that is above a first predetermined threshold;

generate an alert and initiate a first predetermined period of time in response to detection that the amount of power lost is above the first predetermined threshold;

monitor the power transfer during the first predetermined period of time;

determine that the power transfer has not improved during the first predetermined period of time;

reduce a charging rate of a battery of an internal controller of the implantable blood pump in communication with the implanted TETS coil and initiating a second predetermined period of time in response to the determination that the power transfer has not improved during the first predetermined period of time:

monitor the power transfer during the second predetermined period of time;

determine that the power transfer has not improved during the second predetermined period of time; and suspend the power transfer between the external TETS coil and the implanted TETS coil based on the determination that the power transfer has not improved during the second predetermined period of time.

13. The controller of claim 12, wherein the power lost is a function of the implanted TETS coil and the external TETS coil being misaligned while the power transfer is occurring.

14. The controller of claim 12, wherein the power lost is a function of a presence of foreign metallic object between the implanted TETS coil and the external TEST coil while the power transfer is occurring.

15. The controller of claim 12, wherein the power lost exceeding the first determined threshold occurs when a misalignment between the implanted TETS coil and the TETS coil is a distance of 3 centimeters or greater.

16. The controller of claim 12, wherein the power lost exceeding the first determined threshold occurs when a misalignment between the implanted TETS coil and the TETS coil is a distance of 1 centimeters or greater.

17. The controller of claim 12, wherein the first predetermined period of time is 5 minutes, and the second predetermined period of time is 10 minutes.

18. The controller of claim 12, wherein the first predetermined threshold is 200-300 mW.

19. The controller of claim 12, wherein the processing circuitry is configured to generate the alert as a visual, audio, or tactile alert.

* * * * *